United States Patent [19]
Lesher et al.

[11] 4,297,362
[45] Oct. 27, 1981

[54] 4-(3,4-DIAMINOPHENYL)PYRIDINE OR SALTS, AND USE THEREOF AS CARDIOTONIC

[75] Inventors: George Y. Lesher, Schodack; Baldev Singh, East Greenbush, both of N.Y.

[73] Assignee: Sterling Drug Inc., New York, N.Y.

[21] Appl. No.: 173,003

[22] Filed: Jul. 28, 1980

Related U.S. Application Data

[63] Continuation-in-part of Ser. No. 40,210, May 18, 1979, abandoned.

[51] Int. Cl.³ .................... C07D 213/38; A61K 31/44
[52] U.S. Cl. ..................................... 424/263; 546/329
[58] Field of Search ........................ 546/329; 424/263

[56] References Cited

U.S. PATENT DOCUMENTS 3,891,656  6/1975  Fields ............................. 260/290 R
3,994,903  11/1976  Carabateas et al. ............ 260/290 R

OTHER PUBLICATIONS

Cook et al., *Jour. of the Chemical Soc.*, pp. 404–406, (1943).
Coates, *Jour. of the Chemical Soc.*, pp. 406–413, (1943).

*Primary Examiner*—John M. Ford
*Attorney, Agent, or Firm*—Robert K. Bair; B. Woodrow Wyatt

[57] ABSTRACT

4-(3,4-Diaminophenyl)pyridine, a cardiotonic agent, is prepared by reducing 4-(4-amino-3-nitrophenyl)pyridine or preferably by reacting 4-(4-acetylamino-3-nitrophenyl)pyridine or 4-(3-acetylamino-4-nitrophenyl)pyridine with stannous chloride and hydrochloric acid. 4-(3,4-diaminophenyl)pyridine or pharmaceutically-acceptable acid-addition salt thereof is disclosed as the active ingredient in a cardiotonic composition for increasing cardiac contractility and in the method for increasing cardiac contractility in a patient requiring such treatment.

5 Claims, No Drawings

4-(3,4-DIAMINOPHENYL)PYRIDINE OR SALTS, AND USE THEREOF AS CARDIOTONIC

CROSS-REFERENCE TO RELATED APPLICATION

This application is a continuation-in-part of copending application Ser. No. 40,210, filed May 18, 1979, now abandoned.

BACKGROUND OF THE INVENTION (a) Field of the Invention

This invention relates to 4-(3,4-diaminophenyl)pyridine, useful as cardiotonic agent, and to its preparation.

(b) Description of the Prior Art 3-(3,4-Diaminophenyl)pyridine was prepared by Coates et al, J. Chem. Soc. 1943, 406 (413), by catalytic hydrogenation of the corresponding 3-(4-amino-3-nitrophenyl)pyridine using platinum oxide as catalyst. 3-(3,4-Diaminophenyl)pyridine was used as an intermediate to prepare 6-$\beta$-(pyridinyl)-quinoxalines.

2-(3,4-Diaminophenyl)pyridine was prepared by Cook et al., J. Chem. Soc. 1943, 404 (405), by reduction of 2-(4-amino-3-nitrophenyl)pyridine with stannous chloride and hydrochloric acid in ethanol. 2-(3,4-Diaminophenyl)pyridine was used as an intermediate to prepare 6-$\alpha$-(pyridinyl)quinoxalines.

4-(4-Acetylamino-3-nitrophenyl)pyridine and 4-(4-amino-3-nitrophenyl)pyridine are disclosed as intermediates in an multi-step synthesis of 4-(3-nitrophenyl)-pyridine in the Carabateas and Brundage U.S. Pat. No. 3,994,903, issued Nov. 30, 1976.

SUMMARY OF THE INVENTION

In a composition of matter aspect, the invention resides in the compound 4-(3,4-diaminophenyl)pyridine, useful as a cardiotonic agent.

In a preferred process aspect the invention comprises reducing 4-(4-acetylamino-3-nitrophenyl)pyridine or 4-(3-acetylamino-4-nitrophenyl)pyridine with a chemical reducing agent to prepare 4-(3,4-diaminophenyl)-pyridine.

A composition aspect of the invention relates to a cardiotonic composition for increasing cardiac contractility, said composition comprising a pharmaceutically-acceptable carrier and, as the active ingredient thereof, the cardiotonic 4-(3,4-diaminophenyl)pyridine.

In a method aspect, the invention relates to a method for increasing cardiac contractility which comprises the administration of a medicament comprising a pharmaceutically-acceptable carrier and, as the active component thereof, the cardiotonic 4-(3,4-diaminophenyl)-pyridine.

DETAILED DESCRIPTION INCLUSIVE OF PREFERRED EMBODIMENTS

In a composition of matter aspect the invention resides in 4-(3,4-diaminophenyl)pyridine or pharmaceutically-acceptable acid-addition salt thereof. These compounds are useful as cardiotonic agents, as determined by standard pharmacological evaluation procedures.

In a preferred process aspect, the invention comprises reacting 4-(4-acetylamino-3-nitrophenyl)pyridine or 4-(3-acetylamino-4-nitrophenyl)pyridine with stannous chloride and hydrochloric acid to prepare 4-(3,4-diaminophenyl)pyridine.

A composition aspect of the invention resides in the cardiotonic composition for increasing cardiac contractility, said composition comprising a pharmaceutically-acceptable carrier and as the active component thereof, the cardiotonic 4-(3,4-diaminophenyl)pyridine or pharmaceutically-acceptable acid-addition salt thereof.

A method aspect of the invention resides in the method for increasing cardiac contractility in a patient requiring such treatment which comprises administering parenterally in a liquid dosage form to such patient an effective amount of the cardiotonic 4-(3,4-diaminophenyl)pyridine or pharmaceutically-acceptable acid-addition salt thereof.

The 4-(3,4-diaminophenyl)pyridine is useful both in the free base form and in the form of acid-addition salts, and, both forms or within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to form the hydrochloride or lactate. However, other appropriate pharmaceutically-acceptable salts within the scope of the invention are those derived from mineral acids such as sulfuric acid, phosphoric acid and sulfamic acid; and organic acid such as acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the sulfate, phosphate, sulfamate, acetate, citrate, tartrate, methanesulfonate, ethanesulfonate, benzenesulfonate, p-toluenesulfonate, cyclohexysulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of 4-(3,4-diaminophenyl)-pyridine was assigned on the basis of evidence provided by infrared, ultraviolet, nuclear magnetic resonance and mass spectra, by chromatographic mobilities, by the correspondence of calculated and found values for the elementary analyses, and, by methods of its preparation.

The manner of making and using the instant invention will now be generally described so as to enable a person skilled in the art of pharmaceutical chemistry to make and use the same, as follows.

The reduction of 4-(4-amino-3-nitrophenyl)pyridine to produce the corresponding 3,4-diaminophenyl compound can be carried out either by catalytic or chemical reductive means. In practicing the invention, this reduction was conveniently run in a suitable solvent, e.g., acetic acid, in the presence of a hydrogenation catalyst, e.g., platinum oxide, under catalytic hydrogenation conditions at room temperature (about 20° to 25° C.) until the uptake of hydrogen ceased. Other suitable solvents include tetrahydrofuran, dioxane, methanol, ethanol, water (containing a base, e.g., sodium hydroxide, potassium hydroxide, triethylamine, etc.), and the like. Other suitable hydrogenation catalysts include Raney nickel, platinum oxide, and the like. Chemical reducing agents useful in the reduction of the 3-nitro compound to produce the corresponding 3-amino compound include iron and acetic acid, zinc and hydrochloric acid, and the like.

The reaction of 4-(4-acetylamino-3-nitrophenyl)pyridine or 4-(3-acetylamino-4-nitrophenyl)pyridine with stannous chloride and hydrochloric acid to produce 4-(3,4-diaminophenyl)pyridine was unexpected since the expected product would have been 2-methyl-5(or 6)-(4-pyridinyl)benzimidazole. The reaction is conveniently run by heating the reactants in a lower-alkanol, e.g., ethanol, at about 50° to 150° C., preferably on a steam bath. The intermediate 4-(4-acetylamino-3-nitrophenyl)pyridine is known (Carabateas and Brundage, supra) and the intermediate 4-(3-acetylamino-4-nitrophenyl)pyridine is readily prepared by conventional means, as shown hereinbelow.

The following examples will further illustrate the invention without, however, limiting it thereto.

EXAMPLE 1

4-(3,4-Diaminophenyl)pyridine

A mixture containing 115 g. of 4-(4-amino-3-nitrophenyl)pyridine, 1100 ml. of acetic acid and 1.2 g. of platinum oxide was shaken at room temperature under hydrogen under catalytic hydrogenation conditions until the required amount (1.5 mole) of hydrogen was taken up. The catalyst was filtered off and the filtrate concentrated in vacuo under reduced pressure. The residue was titrated with aqueous ammonium hydroxide to liberate the free base form of the product which was recrystallized from ethanol to yield 50.4 g. of 4-(3,4-diaminophenyl)pyridine, m.p. 260°–267° C. with decomposition.

Acid-addition salts of 4-(3,4-diaminophenyl)pyridine are conveniently prepared by carefully adding to a solution of 4-(3,4-diaminophenyl)pyridine in aqueous methanol more than a three molar excess of acid, e.g., concentrated hydrochloric acid, per mole of 4-(3,4-diaminophenyl)pyridine, chilling the mixture and collecting the precipitated salt, e.g., trihydrochloride. Also, the acid-addition salt is conveniently prepared in aqueous solution by adding to water with stirring the appropriate molar equivalent quantities each of 4-(3,4-diaminophenyl)pyridine and the acid, e.g., one molar equivalent each of 4-(3,4-diaminophenyl)pyridine and lactic acid to produce an aqueous solution of 4-(3,4-diaminophenyl)pyridine monolactate.

EXAMPLE 2

A mixture containing 8 g. of 4-(4-acetylamino-3-nitrophenyl)pyridine, 40 ml. of concentrated hydrochloric acid, 15 ml. of ethanol and 27 g. of stannous dichloride dihydrate was stirred for 30 minutes at room temperature and then heated on a steam bath for four hours. The reaction mixture was cooled in an ice bath and the separated solid was collected. The solid was suspended in water and the mixture made basic by adding 35% aqueous sodium hydroxide solution. The yellow solid precipitate was collected, washed with water and dried to yield 3.60 g. of 4-(3,4-diaminophenyl)pyridine, m.p. 255°–258° C. A mixed melting point of this compound and the product obtained above in Example 1 showed no depression.

EXAMPLE 3

To a stirred solution containing 27 g. of stannous dichloride dihydrate, 40 ml. of concentrated hydrochloric acid and 15 ml. of ethanol was added 7.2 g. of 4-(3-acetylamino-4-nitrophenyl)pyridine and the resulting mixture was stirred while heating on a steam bath for two hours and then allowed to stand at room temperature overnight (about fifteen hours). The solid was collected and then treated with 35% aqueous sodium hydroxide solution with stirring for about fifteen minutes. The yellow solid was collected from the resulting mixture to yield 3.4 g. of 4-(3,4-diaminophenyl)pyridine, m.p. 245°–250.3° C. The mass spectra data of this compound obtained by the above procedure is consistent with that of 4-(3,4-diaminophenyl)pyridine.

The above intermediate 4-(3-acetylamino-4-nitrophenyl)pyridine was prepared by the following procedure: To 65 ml. of ice cold 90% $HNO_3$ was added slowly with stirring 16.5 g. of 3-(4-pyridinyl)acetanilide so that the temperature of the reaction mixture did not rise above 5° C. The reaction mixture was maintained below this temperature for six hours and then poured into ice cold water. The resulting mixture was made basic with ammonium hydroxide and the mixture then acidified with acetic acid. The resulting light yellow solid was collected, washed with water, dried and crystallized from ethanol to produce 9.2 g. of 4-(3-acetylamino-4-nitrophenyl)pyridine, m.p. 175°–177° C.

The usefulness of 4-(3,4-diaminophenyl)pyridine or salt as cardiotonic agent is demonstrated by its effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These test procedures are described in the following paragraphs.

Isolated Cat Atria and Papillary Muscle Procedure

Cats of both sexes, weighing 1.5 to 3.5 kg. are each anesthetized with 30 mg./kg. i.p. of sodium pentobarbital and exsanguinated. The chest of each cat is opened, the heart excised, rinsed wiht saline, and the two atria and one or more small, thin papillary muscles from the right ventricle are dissected. The tissues are then transferred to a Petri dish filled with cold modified Tyrode's solution and bubbled with $O_2$. A silver wire is attached to each of two opposite ends of the tissue and one of the wires is hooked to a glass electrode. The preparation is then immediately mounted in a 40 or 50 ml. organ bath filled with modified Tyrode's solution at 37° C. The second wire is attached to a force-displacement transducer and the tension is adjusted to obtain a maximum contractile force (papillary muscle 1.5±0.5 g., left atria 3.0±0.6 g. right atria 4.5±0.8 g.). The transducer is connected to a Grass polygraph and the force and rate of contraction is recorded continuously. The right atrium is beating spontaneously due to the presence of the sino-atrial node, while the left atrium and the papillary muscle are stimulated electrically at a rate of 2 beats/sec. by a suprathreshold rectangular pulse of 0.5 millisecond duration.

The modified Tyrode's solution bathing the preparation is of the following composition (in millimoles): NaCl 136.87, KCl 5.36, NaH$_2$PO$_4$ 0.41, CaCl$_2$ 1.8, MgCl$_2$.6H$_2$O 1.05, NaHCO$_3$ 11.9, glucose 5.55 and EDTA 0.04. The solution is equilibrated with a gas mixture consisting of 95% O$_2$ and 5% CO$_2$ and the pH is adjusted to 7.4 with dilute solution of sodium bicarbonate.

The preparation is left to equilibrate for one hour before any test compound is administered, and the bathing fluid is changed 3 to 4 times during the equilibration time. The 4-(3,4-diaminophenyl)pyridine dissolved in a vehicle (e.g., Tyrode's solution or aqueous solution of acid-addition salt of said compound tested) or the vehicle alone is added to the tissue bath and the full response is recorded. The tissues are washed between doses until predrug control values of rate and force of contraction are obtained. Four to six doses are given to the same preparation over a period of 4 to 6 hours.

When tested by the above-described Isolated Cat Atria and Papillary Muscle Procedure, 4-(3,4-diaminophenyl)pyridine, when tested at a dose of 100 μg./ml. was found to cause significant increase, that is, greater than 25%, in papillary muscle force and a significant increase, that is, greater than 25%, in right atrial force, while causing only a low percentage decrease in right atrial rate.

Anesthetized Dog Procedure

Mongrel dogs of both sexes weighing 9–15 kg. are used in this procedure. The dogs are each anesthetized with 30 mg./kg. i.v. sodium pentobarbital. Supplemental doses of pentobarbital are administered whenever necessary. An intratracheal cannula is inserted and ventilation is carried out by means of a Harvard constant-volume, positive pressure pump using room air. The right femoral artery is cannulated and the cannula is attached to a Statham P23A pressure transducer for the measurement of arterial blood pressure. The right femoral vein is cannulated and used for intravenous administration of compounds to be tested. Pin electrodes are attached to the right forelimb, right hindlimb and left hindlimb, and lead II electrocardiogram is monitored.

A ventro-dorsal incision at the third inter-costal space is made, the heart is exposed and a Walton-Brodie strain gauge is sutured to the wall of the right ventricle for the measurement of cardiac contractile force, that is, cardiac contractility. Aortic and coronary blood flow are measured with a pulsed field electromagnetic flow probe (Carolina Medical Electronics) inserted around the blood vessel in question. Aortic blood flow is used as an approximate index of cardiac output and total peripheral resistance is calculated from aortic flow and mean arterial pressure. All the above parameters measured are recorded simultaneously on a multi-channel Grass polygraph.

The test compound is infused into the femoral vein at a rate of from 0.03 to 0.10 mg./kg./minute until a maximum inotropic effect is obtained. The infusion of the compound is then continued for ten more minutes to maintain an equilibrium at this maximal inotropic effect. At the end of the equilibrium time the infusion is stopped and the rate of decline in cardiac contractile force is observed. Alternatively, the compound is administered intravenously as a single bolus injection of 0.30 to 10 mg./kg.

When tested by the above-described Anesthetized Dog Procedure, 4-(3,4-dimainophenyl)pyridine when administered intravenously at a rate of about 0.1 to 0.3 mg./kg./min. or as a single bolus injection of 10 mg./kg. caused a significant increase, that is, greater than 25%, in cardiac contractile force or cardiac contractility with only low or minimal changes (less than 25%) in heart rate and blood pressure.

The present invention includes within its scope a cardiotonic composition for increasing cardiac contractility, said composition comprising a pharmaceutically-acceptable carrier and, as the active component thereof, the cardiotonic 4-(3,4-diaminophenyl)pyridine or pharmaceutically-acceptable acid-addition salt thereof. The invention also includes within its scope the method for increasing cardiac contractility in a patient requiring such treatment which comprises administering parenterally to such patient an effective amount of said 4-(3,4-diaminophenyl)pyridine or pharmaceutically-acceptable acid-addition salt thereof. In clinical practice said compound or salt thereof will normally be administered parenterally in a wide variety of dosage forms.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for example by filtration through a bacteria-retaining filter, by incorporation of sterilising agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:
1. 4-(3,4-Diaminophenyl)pyridine or pharmaceutically-acceptable acid-addition salt thereof.
2. 4-(3,4-Diaminophenyl)pyridine.
3. A cardiotonic composition for increasing cardiac contractility, said composition comprising a pharmaceutically-acceptable inert carrier and, as the active component thereof, an effective amount of the cardiotonic 4-(3,4-diaminophenyl)pyridine or pharmaceutically-acceptable acid-addition salt thereof.
4. A composition according to claim 3 where the active component is 4-(3,4-diaminophenyl)pyridine.
5. The method for increasing cardiac contractility in a patient requiring such treatment which comprises administering parenterally in a liquid dosage form to such patient an effective amount of the cardiotonic 4-(3,4-diaminiphenyl)pyridine or pharmaceutically-acceptable acid-acceptable salt thereof.

* * * * *

UNITED STATES PATENT AND TRADEMARK OFFICE
CERTIFICATE OF CORRECTION

PATENT NO. : 4,297,362

DATED : October 27, 1981

INVENTOR(S) : George Y. Lesher and Baldev Singh

It is certified that error appears in the above-identified patent and that said Letters Patent are hereby corrected as shown below:

Column 6, claim 5, line 66, "diaminiphenyl" should read -- diaminophenyl --.

Signed and Sealed this

Eighth Day of June 1982

[SEAL]

Attest:

GERALD J. MOSSINGHOFF

*Attesting Officer*  *Commissioner of Patents and Trademarks*